United States Patent [19]

Myers et al.

[11] Patent Number: 5,710,158

[45] Date of Patent: Jan. 20, 1998

[54] ARYL AND HETEROARYL QUINAZOLINE COMPOUNDS WHICH INHIBIT EGF AND/ OR PDGF RECEPTOR TYROSINE KINASE

[75] Inventors: Michael R. Myers, Reading; Alfred P. Spada, Lansdale; Martin P. Maguire, Mont Clare; Paul E. Persons, King of Prussia, all of Pa.

[73] Assignee: Rhone-Poulenc Rorer Pharmaceuticals Inc., Collegeville, Pa.

[21] Appl. No.: 229,886

[22] Filed: Apr. 19, 1994

Related U.S. Application Data

[63] Continuation-in-part of Ser. No. 166,199, Dec. 23, 1993, Pat. No. 5,480,883, which is a continuation-in-part of Ser. No. 988,515, Dec. 10, 1992, abandoned, which is a continuation-in-part of Ser. No. 698,420, May 10, 1991, abandoned.

[51] Int. Cl.$^6$ .................. A61K 31/505; C07D 239/88; C07D 239/93; C07D 239/94
[52] U.S. Cl. .................. 514/259; 544/283; 544/284; 544/287; 544/293
[58] Field of Search .................. 544/293, 283, 544/284, 287; 514/259

[56] References Cited

U.S. PATENT DOCUMENTS

| | | |
|---|---|---|
| 3,715,358 | 2/1973 | Witzel et al. . |
| 3,718,743 | 2/1973 | Shen et al. . |
| 3,971,783 | 7/1976 | Barnish et al. ............ 544/293 |
| 3,985,749 | 10/1976 | Foster . |
| 4,322,420 | 3/1982 | Kobayashi et al. . |
| 4,343,940 | 8/1982 | Kreighbaum ............ 544/283 |
| 4,464,375 | 8/1984 | Kobayashi et al. . |
| 4,465,686 | 8/1984 | Lesher et al. . |
| 4,599,423 | 7/1986 | Lesher et al. . |
| 4,661,499 | 4/1987 | Young et al. . |
| 5,457,105 | 10/1995 | Barker . |
| 5,580,870 | 12/1996 | Barker et al. . |

FOREIGN PATENT DOCUMENTS

| | | |
|---|---|---|
| 0 520 722 | 12/1992 | European Pat. Off. . |
| 0 566 225 A1 | 10/1993 | European Pat. Off. . |
| 0 635 498 A1 | 1/1995 | European Pat. Off. . |
| 1543560 | 4/1979 | United Kingdom . |
| WO92/20642 | 11/1992 | WIPO . |
| WO95/23141 | 8/1995 | WIPO . |

OTHER PUBLICATIONS

Tetahedron, vol. 38, No. 22, pp. 3347–3354 (1982), Tamano, Kodama, Nakajima, Kumada, Minato, Suzuki, Nickel-Phosphine Complex-Catalyzed Grignard Coupling—II Grignard Coupling of, English Original.
Synthesis, pp. 564–565 (Jul. 1986), Yamamoto, Azuma, Mitoh, General Method for Synthesis of Bipyridines: Palladium Catalyzed Cross-Coupling Reaction of, English Original.
Chem. Pharm. Bull., vol. 30, No. 6, pp. 2003–2010 (1982), Yamamoto, Yanagi, Studies on Organometallic Compounds. III. Reaction of Trimethylstannylazines with Acyl Chlorides. A Novel C—C, English Original.
Heterocycles, vol. 23, No. 9, pp. 2375–2386 (1985), Ishikura, Oda, Terashima, A Simple and Regioselective Preparation of 2–or 3–Substituted Quinoline Derivatives Via, English Original.
J. Am. Chem. Soc., vol. 111, No. 3, pp. 877–891 (1989), Stern, Laguren-Davidson, Frank, Gui, Lin, Lu et al., Potential-Dependent Surface Chemistry of 3–Pyridinecarboxylic Acid (Niacin) and Related, English Original.
Chemical Abstract, vol. 84:164632t, p. 453 (1976), Yoshina, Quinoline Derivatives, English Abstract.
Chemical Abstract, vol. 103:123292z, p. 709 (1985), Barker, Huddleston, Clephane, Wood, Holmes, Dehalogenation of 1–Halothienyldi–and 1–Tetrahydroisoquinolines by Sodium Methoxide in, English Abstract.
Chemical Abstract, vol. 108:55860j, p. 704 (1988), Epling, Lin, Sulfur–Containing 2–Arylquinolinemethanols as Potential Antimalarials, English Abstract.
J. Heterocyclic Chem., vol. 20, pp. 1739–1740 (1983), Saeed, Ebraheem, Preparation of Phenylquinoxaline from alpha,alpha–Diaminoketones and, English Original.
Takase et al., Preparation of N–containing heterocyclic compounds as phosphodiesterase inhibitors, Chemical Abstracts, vol. 119:203427t, p. 898 (1993).
Budesinsky et al., Alkoxyquinazolines, Chemical Abstracts, Vo. 86:140078g, p. 569 (1977).
Barnish et al., Quinazoline derivatives, Chemical Abstracts, vol. 82:31349t, p. 503 (1975).
Marquis et al., Antithrombogenic quinazolines, Chemical Abstracts, vol. 77:70423d, p. 59 (1972).
Cronin et al., Hypotensive and bronchodilatory quinolines, isoquinolines, and quinazolines, Chemical Abstracts, vol. 70:68419, p. 397 (1969).
Takase et al., Cyclic GMP Phosphodiesterase Inhibityors. 2. Requirement of 6–Substitution of Quinazoline Derivatives for Potent and Selective Inhibitory Activity, J. Med. Chem., vol. 37, pp. 2106–2111 (1994).
Byford et al., o–Aminophenyl alkyl/aralkyl ketones and their derivativbes, Chemical Abstracts, vol. 111:39292g, p. 594 (1989).
Gopinathan et al., Ruthenium(II) complexes containing nitrogen heterocyclics, Chemical Abstracts, vol. 106:206623w, p. 704 (1987).
Lin et al., Studies on antiarrhythmics, Chemical Abstracts, vol. 96:122728w, p. 695 (1982).
Lederer et al., New synthesis of quazodine–type 7–methoxy–and 6,7–dimethoxyquinazolines, Chemical Abstracts, vol. 84:105533p, p. 575 (1976).

*Primary Examiner*—José G. Dees
*Assistant Examiner*—Mary C. Cebulak
*Attorney, Agent, or Firm*—Raymond S. Parker, III; James A. Nicholson; Martin F. Savitzky

[57] ABSTRACT

This invention relates to the modulation and/or inhibition of cell signaling, cell proliferation, cell inflammatory response, the control of abnormal cell growth and cell reproduction. More specifically, this invention relates to the use of mono- and/or bicyclic aryl or heteroaryl quinazoline compounds in inhibiting cell proliferation, including compounds which are useful protein tyrosine kinase (PTK) inhibitors. The method of treating cell proliferation using said quinazoline compounds and their use in pharmaceutical compositions is described.

14 Claims, No Drawings

ARYL AND HETEROARYL QUINAZOLINE COMPOUNDS WHICH INHIBIT EGF AND/OR PDGF RECEPTOR TYROSINE KINASE

BACKGROUND OF THE INVENTION

This application is a continuation-in-part application of U.S. application Ser. No. 08/166,199, filed Dec. 23, 1993, now U.S. Pat. No. 5,480,883, which is a continuation-in-part of application Ser. No. 07/988,515, filed Dec. 10, 1992, now abandoned which is a continuation-in-part application of U.S. application Ser. No. 07/698,420, filed May 10, 1991 now abandoned and a continuation-in-part application of PCT International Application Serial No. PCT/US92/03736, filed May 6, 1992, which has entered the U.S. National Stage as Ser. No. 08/146,072, filed Nov. 8, 1993.

FIELD OF THE INVENTION

This invention relates to the modulation and/or inhibition of cell signaling, cell proliferation, cell inflammatory response, the control of abnormal cell growth and cell reproduction. More specifically, this invention relates to the use of mono- and/or bicyclic aryl or heteroaryl quinazoline compounds in inhibiting cell proliferation, including compounds which are useful protein tyrosine kinase (PTK) inhibitors.

Normal cellular reproduction is believed to be triggered by the exposure of the cellular substrate to one or more growth factors, examples of which are insulin, epidermal growth factor (EGF) and platelet-derived growth factor (PDGF). Such growth factor receptors are imbedded in and penetrate through the cellular membrane. The initiation of cellular reproduction is believed to occur when a growth factor binds to the corresponding receptor on the external surface of the cellular membrane. This growth factor-receptor binding alters the chemical characteristics of that portion of the receptor which exists within the cell and which functions as an enzyme to catalyze phosphorylation of either an intracellular substrate or the receptor itself, the latter being referred to as autophosphorylation. Examples of such phosphorylation enzymes include tyrosine kinases, which catalyze phosphorylation of tyrosine amino acid residues of substrate proteins.

Many disease states are characterized by the uncontrolled reproduction of cells. These disease states involve a variety of cell types and include disorders such as leukemia, cancer, psoriasis, inflammatory diseases, bone diseases, atherosclerosis and restenosis occuring subsequent to angioplastic procedures. The inhibition of tyrosine kinase is believed to have utility in the control of uncontrolled cellular reproduction, i.e., cellular proliferative disorders.

Initiation of autophosphorylation, i.e., phosphorylation of the growth factor receptor itself, and of the phosphorylation of a host of intracellular substrates are some of the biochemical events which are involved in mediator release mitogenesis and cell proliferation. Autophosphorylation of the insulin receptor and phosphorylation of substrate proteins by other receptors are the earliest identifiable biochemical hormonal responses.

Elimination of the protein tyrosine kinase (PTK) activity of the insulin receptor and of the epidermal growth factor (EGF) receptor by site-directed mutagenesis of the cellular genetic material which is responsible for generation of insulin and EGF results in the complete elimination of the receptor's biological activity. This is not particularly desirable because insulin is needed by the body to perform other biological functions which are not related to cell proliferation. Accordingly, compounds which inhibit the PTK portion of the EGF and/or PDGF receptor at concentrations less than the concentrations needed to inhibit the PTK portion of the insulin receptor could provide valuable agents for selective treatment of cell proliferation disorders.

REPORTED DEVELOPMENTS

It has been reported that the most potent inhibitors of EGF receptors inhibit EGF-induced proliferation of A431/clone 15 cells with little or no effect on the proliferation of such cells when induced by other growth factors. It has been reported also that erbstatin inhibits the autophosphorylation of the EGF receptor in membranes of A431 cells. Higher concentrations of erbstatin are required to inhibit cyclic adenosine 3',5'-monophosphate (cAMP)-dependent protein kinase.

SUMMARY OF THE INVENTION

Inhibitors of $p56^{lck}$, a non-receptor tyrosine kinase, have been shown to be important in intracellular signaling in T-cells. It is assumed that inhibitors of $p56^{lck}$ kinase activity perturb the activation of T-cells and therefore a selective inhibitor could prove useful in the treatment of T-cell mediated conditions such as organ rejection, rheumatoid arthritis or other auto-immune diseases.

The present invention describes compounds which are EGF-R inhibitors prompted and have moderate activity in a $p56^{lck}$ cell-free assay. These compounds do not appear to have any significant serine/threonine kinase inhibitory activity and in addition, compounds within the scope of this invention do not demonstrate significant PDGF-R activity in a cell-free assay. Compounds of this invention are also low µM inhibitors of PDGF-induced mitogenesis which suggests that the quinazolines inhibit other src-like non-receptor kinases involved in the signal transduction pathway.

In accordance with the present invention, there is provided pharmaceutical compositions for inhibiting abnormal cell proliferation in a patient suffering from a disorder characterized by such proliferation comprising the administration to a patient of selective an EGF and/or PDGF receptor inhibiting effective amount of a mono- aryl or hetero- aryl quinazoline compound exhibiting protein tyrosine kinase inhibition activity wherein each aryl group is a ring system containing 0–4 hetero atoms, said compound being optionally substituted or polysubstituted.

Another aspect of the present invention relates to a method of inhibiting abnormal cell proliferation comprising, in admixture with a pharmaceutically acceptable carrier, a pharmaceutically effective amount of a compound of the aforementioned type. Another aspect of this invention comprises compounds useful in the practice of the present method.

With respect to the aspects of this invention, the compounds described by Formula I below constitute a class of the aforementioned mono- and bicyclic aryl or heteroaryl quinazoline compounds for use in the practice of the present invention:

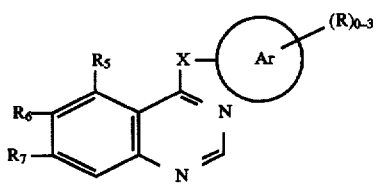

Formula I wherein

Ar is a substituted or unsubstituted mono- or bi-cyclic aryl or heteroaryl ring system of about 5 to about 12 atoms and where each monocyclic ring may contain 0 to about 3 hetero atoms, and each bicyclic ring may contain 0 to about 4 hetero atoms selected from N, O and S provided said hetero atoms are not vicinal oxygen and/or sulfur atoms and where the substituents may be located at any appropriate position of the ring system and are described by R;

X is a bond, O, OCH$_2$, C=C, C≡C, CS, SCH$_2$, NH, NHCH$_2$, NR$_4$ or NR$_4$CH$_2$;

R independently includes R substituents other than hydrogen include alkyl, alkenyl, phenyl, aralkyl, aralkenyl, hydroxy, hydroxyalkyl, alkoxy, alkoxyalkyl, aralkoxy, aryloxy, acyloxy, halo, haloalkyl, nitro, cyano, amino, mono-and di-alkylamino, acylamino, carboxy, carboxyalkyl, carbalkoxy, carbaralkoxy, carbalkoxyalkyl, carbalkoxyalkenyl, aminoalkoxy, amido, mono- and di-alkylamido and N,N-cycloalkylamido, sulfonyl, mono- and di-alkyl sulfonyl, sulfamido, mono- and di- alkyl sulfamido, halophenyl or benzoyl; and R and R together may also form a ketone group.

R$_4$ is alkyl; and

R$_5$, R$_6$ and R$_7$ are independently hydrogen, alkyl, hydroxy, alkoxy, halo, haloalkyl, carboxy or carbalkoxy; or a pharmaceutically acceptable salt thereof.

Preferred Ar monocyclic aryl or heteroaryl rings include substituted or unsubstituted benzene, pyrrole, thiophene, furan, thiazole, imidazole, pyrazole, 1,2,4-triazole, pyridine, 2(1H)-pyridone, 4(1H)-pyridone, pyrazine, pyrimidine, pyridazine, isothiazole, isoxazole, s-triazine, oxazole and tetrazole.

Preferred Ar bicyclic aryl or heteroaryl rings include substituted and unsubstituted naphthalene, naphthyridine, benzofuran, benzothiophene, indole, 2,3-dihydroindole, 1H-indazole, indoline, benzopyrazole, 1,3-benzodioxole, benzoxazole, purine, coumarin, chromone, quinoline, tetrahydroquinoline, isoquinoline, benzimidazole, quinazoline, pyrido[2,3-b]pyrazine, pyrido[3,4-b]pyrazine, pyrido[3,2-c]pyridazine, pyrido[3,4-b]-pyridine, 1H-pyrazole[3,4-d]pyrimidine, pteridine, 2(1H)-quinolone, 1 (2H)-isoquinolone, 1,4-benzisoxazine, benzothiazole, quinoxaline, quinoline-N-oxide, isoquinoline-N-oxide, quinoxaline-N-oxide, quinazoline-N-oxide, benzoxazine, phthalazine, or cinnoline.

More preferred Ar rings include substituted and unsubstituted benzene, pyridine, thiophene, naphthalene, quinoline, indole, 1H-pyrazole[3,4-d]-pyrimidine and Preferred R substituents other than hydrogen include hydrogen, alkyl, alkenyl, hydroxy, alkoxy, halo, haloalkyl, amino, mono-and di-alkylamino, acylamino, carboxy, carbalkoxy, amido, mono- and di-alkylamido, N,N-cycloalkylamido, alkylthio, alkylsulfinyl, alkylsulfonyl or sulphonamido; alkyl, alkenyl, phenyl, aralkyl, aralkenyl, and R and R together may also form a ketone group.

As employed above and throughout this disclosure, the following terms, unless otherwise indicated, shall be understood to have the following meanings:

"Monocyclic aryl or heteroaryl" means a carbocyclic or heterocyclic aromatic ring. Preferred rings include phenyl, thienyl, pyridyl, 2(1H)-pyridonyl, 4(1H)-pyridonyl, furyl, pyrimidinyl, imidazolyl, thiazolyl, oxazolyl and tetrazolyl.

"Bicyclic aryl or heteroaryl" means a bicyclic ring system composed of two fused carbocyclic and/or heterocyclic aromatic rings. Preferred rings include naphthyl, indolyl, benzothienyl, benzofuranyl, quinolinyl, chromonyl, 1(2H)-isoquinolonyl, isoquinolinyl, benzimidazolyl, benzothiazolyl, quinoxalinyl, naphthyridinyl, cinnolinyl, phthalazinyl, pyrido[2,3-b]pyrazinyl, pyrido[3,4-b] pyrazinyl, pyrido[3,2-c]pyridazinyl, pyrido[3,4-b]-pyridinyl, pteridinyl, and quinazolinyl.

"Alkyl" means a saturated aliphatic hydrocarbon, either branched- or straight-chained. Preferred alkyl is "lower-alkyl" having about 1 to about 6 carbon atoms. Examples of alkyl include methyl, ethyl, n-propyl, isopropyl, butyl, sec-butyl, t-butyl, amyl and hexyl.

"Alkoxy" refers to an alkyl-O-group. Preferred alkoxy groups include methoxy, ethoxy, propoxy and butoxy.

"Aryloxy" refers to an aryl-O-group. The preferred aryloxy group is phenoxy.

"Aralkyl" means an alkyl group substituted by an aryl radical. The preferred aralkyl groups are benzyl or phenethyl.

The preferred aralkoxy groups are benzyloxy and phenethoxy.

The preferred acyloxy groups are acetoxy and benzyloxy;

"Halo" means halogen. Preferred halogens include chloride, bromide and fluoride.

The preferred haloalkyl group is trifluoromethyl.

The more preferred compounds of this invention include those compounds of Formula I where Ar is phenyl or naphthyl;

R is hydrogen, alkyl, alkoxy, hydroxy, halo or trifluoromethyl.

X is a bond, NH or NR$_4$; and

R$_5$, R$_6$ and R$_7$ are independently hydrogen or alkoxy.

The most preferred compounds are those described where Ar is phenyl;

X is NH or NMe; and

R$_5$, R$_6$ and R$_7$ are independently hydrogen or methoxy.

It is intended that N-oxides of the above described aminoquinazolines are encompassed within the scope of this invention.

Compounds within the scope of this invention inhibit the growth factor induced autophosphorylation of PDGF and/or EGF receptors. It is believed that therapeutically useful PTK inhibiting compounds should not have appreciable activity as inhibitors of serine or threonine kinase systems. In addition these compounds should inhibit growth factor-induced cell proliferation. Compounds meeting these criteria are of considerable value and are particularly useful in the practice of the present invention. Compounds exhibiting selectivity for either of the above receptors are described herein.

More particularly the compounds of this invention are specific to inhibiting the growth factor.

Special embodiments of this invention inhibiting the growth factor. include the following:

A. Compounds of Formula I where:

X is NR$_4$, S or O, the inhibiting cell proliferation is especially characterized by CSF-1 activity.

B. Compounds of Formula I where:

X is NH, the inhibiting cell proliferation is especially characterized by lck/EGF activity.

C. Compounds of Formula I where:
   X is NH, S, O or $OCH_2$ and Ar is a bicyclic aryl, substituted bicyclic aryl, bicyclic heteroaryl or substituted bicyclic heteroaryl, the inhibiting cell proliferation is especially characterized by EGF activity. Where Ar is α-naphthyl is especially preferred.

D. Compounds of Formula I where:
   X is a bond and Ar is phenyl, indolyl, pyrrolyl, thienyl, pyridyl, naphthyl, a bicyclic aryl, a bicyclic heteroaryl or substituted phenyl, indolyl, pyrrolyl, thienyl, pyridyl, naphthyl, bicyclic aryl, bicyclic heteroaryl, the inhibiting cell proliferation is especially characterized by lck activity. Where bicyclic heteroaryl or substituted bicyclic heteroaryl is 1,3-benzodioxole or 1,4-benzodioxin is especially preferred.

E. Compounds of Formula I where:
   X is NH, $R_6$ and $R_7$ are alkoxy and Ar is phenyl having at least one substituent in the 3, 4 and/or 5 positions of hydroxy or alkoxy, the inhibiting cell proliferation is especially characterized by lck activity.

The compounds of this invention may be useful in the form of the free base, in the form of salts and as a hydrate. All forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

The corresponding acid addition salts comprise the following: hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The compounds of this invention may be prepared by employing procedures known in the literature starting from known compounds or readily preparable intermediates. Exemplary general procedures follow.

In general the compounds useful for the method of inhibiting cell proliferation may be prepared by the coupling reaction of a palladium catalyzed aryl or heteroarylstannane with an aryl or heteroarylhalide or triflate.

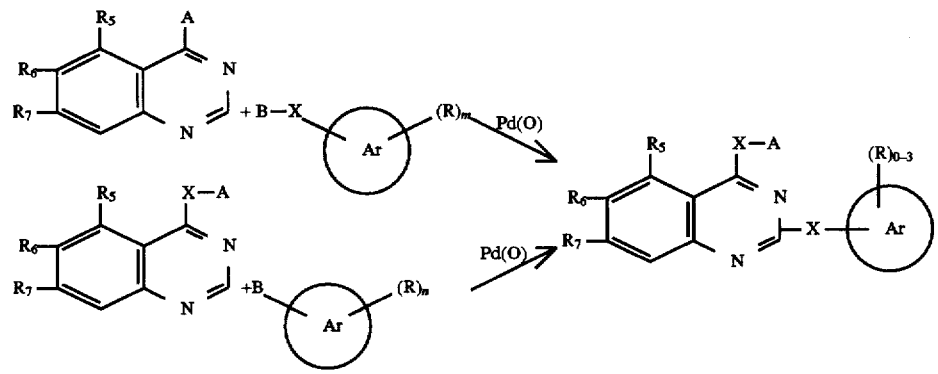

where A is halogen or triflate and B is trialkylstannane and R is as previously described.

The 4-haloquinazoline starting materials are prepared in the classical way using anthranilic acid derivatives and formamide at reflux to provide the intermediate quinazolinones. Subsequent treatment with $POCl_3$ at about 110° C. for about two hours provides the chloroquinazolines. The final products are prepared via a condensation with the appropriate aniline derivative in a polar solvent such as ethanol. In the case of the phenoxy or thiophenoxy derivatives, the metal salt (preferably Na) is prepared and refluxed for several hours with the appropriate haloquinazoline in a solvent such as THF.

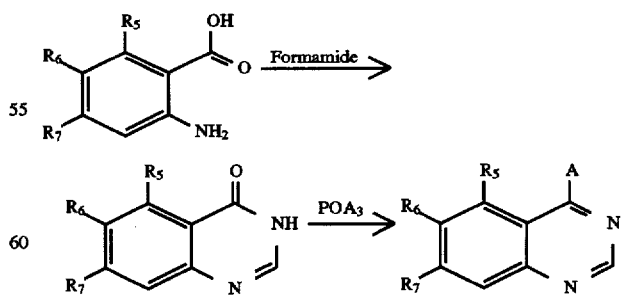

Other triflates suitable for coupling with the aryl and heteroarylstannanes may be prepared in a similar manner.

Triflates may also be prepared from 4(1H) quinolones as shown by the following.

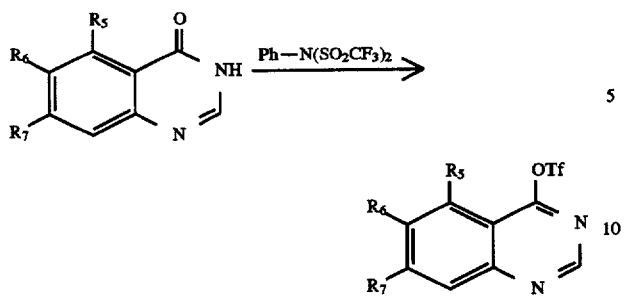

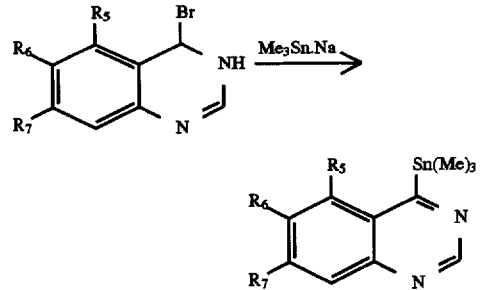

The triflimide such as used in the above reaction may also be used to prepare compounds having a particular substitution such as the following compound.

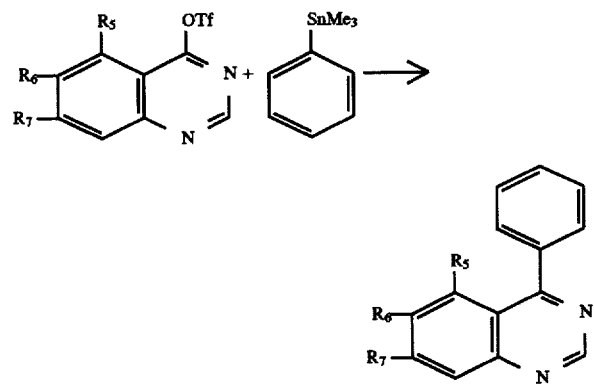

The aryl and heteroarylstannanes may be prepared from the corresponding halide (preferably bromide or iodide) by conversion to the aryllithium (by reaction with t-butyllithium at decreased temperatures, preferably about −78° C. followed by reaction with a halotrialkylstannane.

Of course these products may also be prepared in the reverse manner using the aryl or heteroarylhalides with the the corresponding stannane.

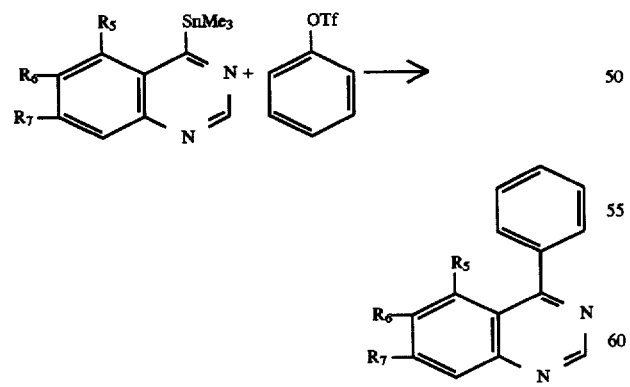

The quinazoline stannanes intermediates may be prepared by the action of trimethyltin sodium on aryl halides as described in Chem. Pharm. Bull. 1982, 30, 1731–1737:

The preparation of the compounds useful in this invention are described in Applicants' copending application U.S. Ser. No. 08/166,199, filed Dec. 10, 1993, of which this application claims priority. U.S. Ser. No. 08,166,199 is hereby incorporated herein by reference.

Further, the following examples are representative of the processes used to synthesis the compounds of this invention.

The below examples and those described in U.S. Ser. No. 08/166,199 may be followed to prepare any of the desired compounds of this invention. A representative list of compounds which may be prepared is shown below.

EXAMPLE 1

4-m-chlorophenoxy)-6,7-dimethoxyquinazoline

THF (5 ml) and NaH (60% disp in oil, approx. 28 mg) is added to a dry flask maintained under inert atmosphere at room temperature. m-Chlorophenol (0.09 g) is added as a soln. in THF (1 mL) and stirring is continued until the solution became clear. 4-Chloro-6,7-dimethoxyquinazoline is added all at once (as the solid) and stirring was maintained overnight at RT. The solution is partitioned between $CH_2CL_2$ and 5% NaOH. The organic layer is washed with brine, dried ($Na_2SO_4$) and concentrated. Flash column chromatography (40% EtOAc/Hex) provided the pure compound. An analytical sample is obtained by recrystallization from EtOAc/Hex to provide 4-m-chlorophenoxy)-6,7-dimethoxyquinazoline (0.05 g, white needles, m.p. 152°–153° C.

EXAMPLE 2

4-(1-methylsulphonylindol-3-yl)-6,7-dimethoxyauinazoline

Step A N-methylsulfonyl-3-trimethylstannylindole

A solution of 5 g (15.57 mmol) of N-methylsulfonyl-3-iodoindole (5.1 g; 15.57 mmol) of hexamethylditin and 0.89 g (0.78 mmol) of Pd (PPh$_3$)4 in 75 mL of dry toluene is flushed thoroughly with nitrogen and heated to 90° C. for 4 hours. The mixture is then evaporated and chromatographed on silica gel (eluting with hexane and then with 10% ethyl acetate/hexane to give N-methylsulfonyl-3-trimethylstannylindole which is used directly in the next step.

Step B 4-(1 -methylsulphonylindol-3-yl)-6,7-dimethoxyquinazoline

A solution of 1.33 g (4.01 mmol) of N-methylsulfonyl-3-trimethylstannylindole, 750 mg (3.34 mmol) of 4-chloro-6,7-dimethoxyquinazoline and 0.19 g (5 mol % 0.16 mmol) of Pd (PPh$_3$)$_4$ in 10 ml of dry dimethylformamide is flushed thoroughly with nitrogen and heated to 90° C. for 12 hours. The reaction mixture is diluted with methylene chloride washed with 10% ammonium hydroxide and stirred vigorously and then washed with water and the combined organics are washed with brine (75 mL), dried (MgSO₄) and evaporated to dryness. Recrystallized from ethyl acetate yields 4-(1-methylsulphonylindol-3-yl)-6,7-dimethoxyquinazoline (m.p. >220° C.).

The above examples may be followed to prepare any of the desired compounds of this invention. A representative list of compounds which may be prepared are shown below.

6,7-dimethoxy-4-naphthalen-2-ylethynylquinazoline, m.p. 158°–161° C.
4-(4-hydroxyphenyl)-6,7-dimethoxyquinazolinehydrochloride, m.p. >270° C. (dec)
4-(naphthalen-1-yl)-6,7-dimethoxyquinazoline, m.p. 144°–147° C.
4-(naphthalen-2-yl)-6,7-dimethoxyquinazoline, m.p. 115°–118° C.
4-phenylacetylenyl-6,7-dimethoxyquinazoline, m.p. 146°–148° C.
4-(3-fluoro-4-methoxyphenyl)-6,7-dimethoxyquinazoline, m.p. 207°–210° C.
4-(3-phenylphenyl)-6,7-dimethoxyquinazoline, m.p. 160°–163° C.
4-(2-phenylethylenyl)-6,7-dimethoxyquinazoline, m.p. 168°–169° C.
4-(2-methoxypyridin-5-yl)-6,7-dimethoxyquinazoline, m.p. 175°–176° C.
4-(1-benzyl-indol-3-yl)-6,7-dimethoxyquinazoline, m.p. 148°–150° C.
4-(indol-3-yl)-6,7-dimethoxyquinazoline, m.p. >240° C. (dec)
4-(1-methylindol-3-yl)-6,7-dimethoxyquinazoline hydrochloride, m.p. >230° C. (dec)
4-(1-methylsulphonylindol-3-yl)-6,7-dimethoxyquinazoline, m.p. >220° C. (dec)
4-(4-phenylpiperidin-1-yl)-6,7-dimethoxyquinazoline, m.p. 150°–151° C.
4-[4-(3-chlorophenyl)piperazin-1-yl]-6,7-dimethoxyquinazoline, m.p. 155°–156° C.
4-(N-methyl-8,4,5-trimethoxyanilino)-6,7-dimethoxyquinazoline, m.p. 149°–151° C.
(±)-4-(2-methyl-1,2,3,4-tetrahydroquinolin-1-yl)-6,7-dimethoxyquinazoline hydrochloride, m.p. 198°–201° C. (dec)
4-(1,2,3,4-tetrahydroquinolin-1-yl)-6,7-dimethoxyquinazoline hydrochloride, m.p. 195°–197° C. (dec)
4-(N-methyl-4-methoxy-anilino)-6,7-dimethoxyquinazoline hydrochloride, m.p. 202°–205° C.
4-(N-methyl-4-chloro-anilino)-6,7-dimethoxyquinazoline hydrochloride, m.p. 220°–222° C.
4-(2,3-dihydroindol-1-yl)-6,7-dimethoxyquinazoline hydrochloride, m.p. 226°–229° C. (dec)
(6,7-dimethoxyquinazolin-4-yl) methyl-(3-trifluoromethylphenyl)amine hydrochloride, m.p. 240°–243° C.
(3-chlorophenyl)-(6,7-dimethoxyquinazolin-4-yl) methylamine hydrochloride, m.p. 235°–237° C.
(3-chlorophenyl)methylquinazolin-4-yl-amine hydrochloride, m.p. 233°–235° C.
6,7-dimethoxy-4-naphthalen-1-yl-ethynylquinazoline, m.p. 175°–177° C.
4-(thien-3-yl)-6,7-dimethoxyquinazoline m.p. 148.5°–151.5° C.
4-benzyl-6,7-dimethoxyquinazoline m.p. 122.5°–125° C.
(6,7-dimethoxyquinazolin-4-yl)-5-indazolylamine hydrochloride, m.p. 261°–263° C. (dec)
N-phenyl-N-(6,7,8-trimethoxyquinazolin-4-yl)methylamine, m.p. 122.5°–124.5° C.
(6,7-dimethoxyquinazolin-4-yl)-N-phenylethylamine hydrochloride, m.p. 227°–230° C. (dec)
benzyl-(6,7-dimethoxyquinazolin-4-yl)phenylamine hydrochloride, m.p. 269°–271° C.
(6-chloroquinazolin-4-yl)methylphenylamine, m.p. 106°–108° C.
(3-chloro-phenyl)-(6,7-dimethoxyquinazolin-4-yl)ethylamine hydrochloride, m.p. 261°–263° C.
(6,7-dimethoxyquinazolin-4-yl)methyl-p-tolyl-amine hydrochloride, m.p. 230°–234° C. (dec)
benzyl-(6,7-dimethoxyquinazolin-4-yl)amine, m.p. 220°–225° C.
(4-methoxybenzyl)-(6,7-dimethoxyquinazolin-4-yl)amine, m.p. 194°–198° C.
(3,5-dimethoxybenzyl)-(6,7-dimethoxyquinazolin-4-yl)amine hydrochloride, m.p. 265°–269° C.
4-(3,4,5-trimethoxyphenoxy)-6,7-dimethoxyquinazoline m.p. 228°–232° C.
(quinazolin-4-yl)-N-phenyimethylamine hydrochloride, m.p. 242°–246° C. (dec)
(6,8-dimethylquinazolin-4-yl)-N-phenylmethylamine, m.p. 120°–121° C.
(6,7-dimethoxyquinazolin-4-yl)-4-morpholin-4-yl-phenyl)amine hydrochloride, m.p. 231°–235° C. (dec)
4-(3-methoxythiophenoxy)-6,7-dimethoxyquinazoline, m.p. 139.5°–141.5° C.
4-[N-(5-indanyl)amino]-6,7-dimethoxyquinazoline hydrochloride, m.p. 244°–246° C. (dec)
4-(3-chlorothiophenoxy)-6,7-dimethoxyquinazoline, m.p. 152°–153.5° C.
4-(pyrazol-3-ylamino)-6,7-dimethoxyquinazoline hydrochloride, m.p. 262°–264° C. (dec)
4-(3,6-dioxananilino)-6,7-dimethoxyquinazoline hydrochloride, m.p. 267°–269° C. (dec)
6,7-dimethoxy-4-(α-naphthylamino)quinazoline hydrochloride, m.p. >250° C.
6,7-dimethoxy-4-(β-naphthylamino)quinazoline hydrochloride, m.p. >250° C.
4-(cyclohexylanilino)-6,7-dimethoxyquinazoline, m.p. 239°–244° C.
4-(3,4,5-trimethoxyanilino)-6,7-dimethoxyquinazoline hydrochloride, m.p. 260°–265° C.
6,7-dimethoxy-4-(N-methylanilino)quinazoline hydrochloride, m.p. >230° C.
4-(3-chlorophenoxy)-6,7-dimethoxyquinazoline, m.p. 152°–153° C.
6,7-dimethoxy-4-(1-naphthylthio)-quinazoline, m.p. 174.5°–176.5° C.
6,7-dimethoxy-4-(2-naphthylthio)-quinazoline, m.p. 178°–179° C.
6,7-dimethoxy-4-(1-naphthyloxy)-quinazoline, m.p. 214°–215.5° C.
6,7-dimethoxy-4-(2-naphthyloxy)-quinazoline, m.p. 169°–170° C.
(6,7-Dimethoxy-quinolazolin-4-yl)-2-naphthyl-ethylamine hydrochloride, m.p. 236°–239° C. (dec)
6,7-dimethoxy-4-(naphthalene-2-sulfinyl)-quinazoline, m.p. 182.5°–185° C.
6,7-dimethoxy-4-(naphthalene-2-sulfonyl)-quinazoline Preparation of Pharmaceutical Compositions and Pharmacological Test Section Compounds within the scope of this invention exhibit significant activity as protein tyrosine kinase inhibitors and possess therapeutic value as cellular antiproliferative agents for the treatment of certain conditions including psoriasis, atherosclerosis and restenosis injuries. It is expected that the invention will be particularly applicable to the treatment of atherosclerosis. With regard to the treatment of some conditions, for example, atherosclerosis, certain people may be identified as being at high risk, for example, due to genetic, environmental or historical factors. Compounds within the scope of the present invention exhibit the modulation and/or inhibition of cell signaling, cell proliferation, cell inflammatory response, the control of abnormal cell growth and cell reproductioncan and can be used in preventing or delaying the occurrence or reoccurrence of such conditions or otherwise treating the condition.

To determine the effectiveness of compounds of this invention, the following pharmacological tests described below, which are accepted in the art and recognized to correlate with pharmacological activity in mammals, are utilized. Compounds within the scope of this invention have been subjected to these various tests, and the results obtained are believed to correlate to useful cellular antiproliferative activity. The below described tests are useful in determining the EGF receptor kinase, PDGF receptor kinase and insulin receptor kinase inhibition activities of compounds disclosed herein. The results of these tests are believed to provide sufficient information to persons skilled in the pharmacological and medicinal chemistry arts to determine the parameters for using the studied compounds in one or more of the therapies described herein.

EGF-Receptor Purification

EGF-receptor purification is based on the procedure of Yarden and Schlessinger. A431 cells are grown in 80 cm$^2$ bottles to confluency ($2\times10^7$ cells per bottle). The cells are washed twice with PBS and harvested with PBS containing 11.0 mmol EDTA (1 hour at 37° C., and centrifuged at 600g for 10 minutes. The cells are solubilized in 1 ml per $2\times10^7$ cells of cold solubilization buffer (50 mmol Hepes buffer, pH 7.6, 1% Triton X-100, 150 mmol NaCl, 5 mmol EGTA, 1 mmol PMSF, 50 µg/ml aprotinin, 25 mmol benzamidine, 5 µg/ml leupeptic, and 10 µg/ml soybean trypsin inhibitor) for 20 minutes at 4° C. After centrifugation at 100,000g for 30 minutes, the supernatant is loaded onto a WGA-agarose column (100 µl of packed resin per $2\times10^7$ cells) and shaken for 2 hours at 4° C. The unabsorbed material is removed and the resin washed twice with HTN buffer (50 mmol Hepes, pH 7.6, 0.1% Triton X-100, 150 mmol NaCl), twice with HTN buffer containing 1M NaCl, and twice with HTNG buffer (50 mmol Hepes, pH 0.1% Triton X-100, 150 mmol NaCl, and 10% glycerol). The EGF receptor is eluted batchwise with HTNG buffer containing 0.5 M N-acetyl-D-glucosamine (200 µl per $2\times10^7$ cells.). The eluted material is stored in aliquots at −70° C. and diluted before use with TMTNG buffer (50 mmol Tris-Mes buffer, pH 7.6, 0.1% Triton X-100, 150 mmol NaCl, 10% glycerol).

ATP and EGF Dependence of Autophosphorylation

WGA-purified EGF receptor from A431 cells (0.5 µg/assay is activated with EGF (0.85 µM) for 20 minutes at 4° C. The assay is performed at 15° C. and initiated by addition of Mg(Ac)$_2$ (60 mmol), Tris-Mes buffer, pH 7.6 (50 mmol), [$^{32}$P]ATP (carrier free, 5 µCi/assay), and increasing concentrations of nonradioactive ATP. The assay is terminated after 10-sec by addition of SDS sample buffer. The gel samples are run on a 6% SDS polyacrylamide gel. The gel is dried and autoradiographed as described above. The relevant radioactive bands are cut and counted in the Cerenkov mode. The K$_m$ for ATP determined in this fashion is found to be 7.2 µ(M. With use of the 10-sec assay protocol, the EGF concentration dependence of EGF-RK autophosphorylation is determined.

Inhibition of EGF-R Autophosphorylation

A431 cells are grown to confluence on human fibronectin coated tissue culture dishes. After washing 2 times with ice-cold PBS, cells are lysed by the addition of 500 µl/dish of lysis buffer (50 mmol Hepes, pH 7.5, 150 mmol NaCl, 1.5 mmol MgCl$_2$, 1 mmol EGTA, 10% glycerol, 1% triton X-100, 1 mmol PMSF, 1 mg/ml aprotinin, 1 mg/ml leupeptin) and incubating 5 minutes at 4° C. After EGF stimulation (500 µg/ml 10 minutes at 37° C.) immunoprecipitation is performed with anti EGF-R (Ab 108) and the autophosphorylation reaction (50 µl aliquots, 3 µCi [γ-$^{32}$P] ATP) sample is carried out in the presence of 2 or 10 µM of compound of the present invention, for 2 minutes at 4° C. The reaction is stopped by adding hot electrophoresis sample buffer. SDA-PAGE analysis (7.5% els) is followed by autoradiography and the reaction is quantitated by densitometry scanning of the x-ray films.

In order to test the present compounds for selective inhibition, the procedure is repeated using PDGF stimulation in place of EGF stimulation. "IC$_{50}$," as used below refers to the concentration of inhibitor mM) at which the rate of autophosphorylation is halved, compared with media containing no inhibitor.

Inhibition of PDGF-R Autophosphorylation

Lysate from NIH 3T3 cells is diluted one-third in Triton-free buffer and stimulated with 10 ng/ml PDGF for 30 minutes at 4° C. The equivalent of $\frac{1}{15}$ of a 175-cm$^2$ plate; of lysate is used per sample. The stimulated lysate is then immunoprecipitated with rabbit polyclonal anti-PDGF-receptor antibodies raised against a synthetic peptide from the COOH-terminal region (areinc acids 1094–1106) or the human PDGF-receptor β-subunit and added to increasing concentrations of test compound of the present invention. After 10 minutes at 4° C., 10 µCi of [γ-$^{32}$P]ATP are added and further incubated for 10 minutes at 4° C. Samples are separated by SDS-PAGE on 6% gels.

Inhibition of Cell Proliferation as Measured by Inhibition of DNA Synthesis

EGF receptor overexpressing (HER14) cells are seeded at $1\times10^5$ cells per well in 24-well Costar dishes pre-coated with human fibronectin (by incubating for 30 minutes at room temperature with 10 µg/0.5 ml/well). The cells are grown to confluence for 2 days. The medium is changed to DMEM containing 0.5 calf serum for 36–48 hours and the cells are then incubated with EGF (Toyobo, New York, N.Y.) (20 ng/ml), PDGF (Amgen) (20ng/ml) or serum (10% calf serum, FOS) and different concentrations of the compound of the present invention. [$^3$H] thyroidinc, (NEN, Boston, Mass.) is added 16–24 hours later at 0.5 µCi/ml for 2 hours. TCA precipitable material is quantitated by scintillation counting (C- Results of this assay are determined. "IC$_{50}$" of the concentration of inhibitor (nM) at which [$^3$H]thymidine incorporation is halved, compared with media containing no buffer is calculated As FCS contains a broad range of growth factors, the IC$_{50}$ values for PDGF should be lower than for FCS, indicating that the compounds of the present invention do not act as general inhibitors.

These results indicate that compounds within the scope of the invention inhibit the EGF and/or PDGF growth factor receptors selectively.

Cell Culture

Cells termed HER 14 and K721A (=DK) are prepared by transfecting NIH3T3 cells (clone 2.2) (From C. Fryling, NCI, NIH), which lack endogenous EGF-receptors, with cDNA constructs of wild-type EGF-receptor or mutant EGF-receptor lacking tyrosine kinase activity (in which Lys 721 at the ATP-binding site is replace by an Ala residue, respectively). All cells are grown in DMEM with 10% calf serum (Hyclone, Logan, Utah).

Further tests which show the effectiveness and selectivity of compounds of this invention to inhibit cell proliferation are as follows.

CSF-1R CELL-FREE AUTOPHOSPHORYLATION ASSAY

For a regular 28 tube assay (14 samples per 15 well gel):

In 2 ml eppendorf tube: 140 mg protein A sepharose (5 mg/sample) Swell in 20 mM Hepes pH 7.5 and wash 2× in Hepes Add 280 λα-CSF-1R (from rabbit 3:C1-3-?) 20 min RT shaking Wash 3× in HNTG pH 7.5:

20 mM Hepes
150 mM NaCl
0.1% triton X-100
10% glycerol

In 15 ml tube: 2.8 ml lysate (100 λ/sample of lysate made from unstarved, subconfluent cfmY cells)

lysis buffer: 20 mM Hepes
1.5 mM $MgCl_2$
150 mM NaCl
1 mM EGTA
10% glycerol
1% triton X-100

Protease inhibitors added fresh:

PMSF: 8 mg/ml=2500× in 100% ETCH, store frozen, add 100λ/10 ml lysis buffer

Aprotinin: 10 mg/ml=250× in $H_2O$, store frozen (expires in about 6 months), add 40λ/10 ml lysis buffer Leupeptin: 1 mg/ml=250× in $H_2O$, store frozen (expires in about 6 months), add 40λ/10 ml lysis buffer Add washed beads to stimulated lysate and incubate 90 min 4° C. on rotator or shaking (anywhere from 1 to 2.5 hours OK)

Meanwhile:

prepare 28 compound tubes:
make 40 mM solutions of compounds in 100% DMSO
make serial dilutions in 50 mM Tris pH 7.5+10 mM $MnCl_2$ aliquot 10λ compound solution into each 1 ml eppendoff reaction tube waiting on ice, control blanks get 10λ, buffer Wash beads 1× HNTG, 2× 10 mM Tris pH 7.5 (can transfer beads to 2 ml eppendorf tube for washing)

Remove all liquid with gel loading pipette tip or Hamilton syringe

Add back 560λ 50 mM Tris pH 7.5+10 mM $MnCl_2$ (20λ/sample)

Dole out into waiting reaction tubes (approx. 28λ/tube using large bore tip) Vortex, incubate 10 min on ice Add 10λ ATP solution:
312λ 50 mM Tris pH 7.5+10 mM $MnCl_2$
2.7λ cold ATP (stock of 10 mM in 50 mM Tris=20 µM final)
351 $^{32}$P-ATP (10 µCi/sample)
Vortex, incubate 10 min on ice
Add 45λ 2× SDS-sample buffer, heat 95° C. 6 min
7.5% SDS-PAGE, fix, dry, expose (usually 4 hrs)

*Note: it is important to keep lysate cold at all times: when thawing, don't use water which is too warm and use cold buffer for wash steps.

lck Kinase: Immunoprecipitated from Jurkat lysate[5,6]

A. Jurkat cells (human T-cell leukemia, ATCC clone #E6-1) are grown in suspension in RPMI 1640 medium with 10% fetal calf serum, 100 U/ml penicillin/streptomycin, and 2 mM L-glutamine in a 37° C. incubator at 5% $CO_2$.

B. Cells are grown to 1–1.5×10$^6$ cells/ml media, pelleted by centrifugation, and lysed in lysis buffer at 10$^8$ cells/mi buffer (50 mM tris (pH 8), 150 mM NaCl, 5 mM EDTA, 10% glycerol, and 1% NP-40, to which fresh protease and phosphatase inhibitors are added as described above for A431 lysate). Lysates stored at −70° C.

C. Immunoprecipitation [#5264: 12]: 3–4 mg Protein-A sepharose/sample washed 2× 20 mM Hepes (pH 7.5). 1 µl α-lck antibody (prepared as polyclonals in rabbits using a peptide antigen corresponding to the N-terminal region of human lck) per sample added to the Protein-A and shaken 20 min at room temperature. After washing 3× HNTG, lysate from 2×10$^6$ cells is added to each sample, rotated 2 hr at 4° C., then washed 3× HNTG (2nd wash containing 0.5 N NaCl). If all samples contain identical concentrations of the enzyme, then the immuno-precipitation can be done in bulk and alloquoted to appropriate numbers of tubes prior to assay set-up.

D. Compound screening in the cell-free lck kinase assay [#5264:12]: RPR compounds (40 mM stocks in DMSO) are initially screened at concentrations of 10 and 100 µM in samples containing lck immuno-precipitated from 2×10$^6$ cells, 5 µM cdc2 (a p34$^{cdc2}$-derived synthetic peptide (N6-20) prepared by R. Howk, RPR)[7], 5 mM $MnCl_2$, 5 µM ATP and 30 µCi g$^{32}$P-ATP (6000 Ci/mmol, NEN) in 20 mM hepes (pH 7.5) for 5 min at 30° C. Samples are analyzed by 5–15% SDS-PAGE and autoradiography as described for EGFR kinase assays.

E. Intact cell activation/inhibition studies[8,9] [#5264:31] :~5×10$^7$ cells per sample in 1 ml media are activated with either 10 µg a-OD3 (clone Cris 7, Biodesign) for 1 min at 37° C. or 20 ng PMA and 10 µg PHA for 20 min at 37° C. in the presence and absence of compound (added earlier so that the total time of compound incubation is 30 min). Incubations are terminated by centrifugation and lysis (as described). Samples are analyzed by immunoprecipitation (aPY (100 µl/10$^8$ cells), a-PLC (100 µl/10$^8$ cells), or a-zeta (20 µl/10$^8$ cells)), followed by SDS-PAGE and western blotting onto nitrocellulose and immunoblotting using RC20 recombinant aPY-HRP Transduction Labs) and EOL (Amersham).

cAMP-dependent Protein Kinase (PKA) Assay[10]

Selectivity assay for compounds is performed as follows. Each sample contains 0.4 pmolar units PKA (from rabbit muscle, Sigma), 1 µM cAMP, 50 µM Tris-HCL (pH7), 10 mM MgAc, 50 µg BSA, 16 µM Kemptide substrate (specific cAMP kinase phosphate acceptor whose sequence corresponds to the pig liver pyruvate kinase phosphorlyation site), 16 µM ATP, 16 µCi $^{32}$P-ATP (6000 Ci/mmol, NEN), +/−compound and d$H_2O$ to a final volume of 200 µl. Reactions proceed for 5 min. at 30° C., and are terminated by the addition of 100 µl 375 mM $H_3PO_4$. 50 µl each sample spotted onto Whatman P81 phosphocellulose filters, which are washed 3× (15 min.) in 75 mM $H_3PO_4$, followed by an acetone rinse and dry (Cerenkov) counting.

In view of the results of the above test, compounds of the present invention can be shown to be selective.

The preferred class of compounds exhibiting CSF-1 inhibition and lck Kinase inhibition are the 6,7-dialkoxy quinazolines, and most preferred are the 4-arylamino, 6,7-dimethoxyquinazolines. The most preferred lck inhibitory compound is 4-(3,4,5-trimethoxyphenylamino) -6,7-dimethoxyquinazoline, (m.p. 260°–265° C. (HCl)), which is prepared according to the procedure described in Example 36 using 1.6 g of 3,4,5-trimethoxyaniline and 0.2g of 4-chloro,-6,7-dimethoxyquinazoline, under similar reaction conditions. The most preferred CSF-1 inhibitory compound is 4-(N-methyl, N-phenylamino)-6,7-dimethoxyquinazoline, (m.p >230° C.(HCl)), which is prepared according to the procedure described in Example 36 using 140 mg of N-methylaniline and 300 mg of 4-chloroquinazoline, under similar reaction conditions.

The following tables show examples of representative compounds of this invention and their test results as determined by the above inhibition of PDGF-R cell-free autophosphorylation procedure.

| Structure | Ick activity IC$_{50}$ (μM) | EGF activity IC$_{50}$ (μM) |
|---|---|---|
| [quinazoline with 5,6-dimethoxy and CH(CH$_2$Ph) substituent] | 100 | ≦0.5 |
| [quinazoline with NH-(3-chlorophenyl)] | ≦100 | 0.05–0.1 |
| [quinazoline with NH-(3-methoxyphenyl)] | ≦100 | 0.05 |
| [6,7-dimethoxyquinazoline with NH-(3-chlorophenyl)] | 5 | 0.03 |
| [6,7-dimethoxyquinazoline with NH-(3-methoxyphenyl)] | 5 | 0.05 |

| Structure [6,7-dimethoxyquinazoline core] | Ick activity IC$_{50}$ (μM) | EFG activity IC$_{50}$ (μM) |
|---|---|---|
| [NH-(3,5-dimethylphenyl)] | >100 | — |

-continued
| | | |
|---|---|---|
| 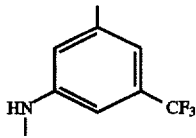 | >10–<100 | — |
| 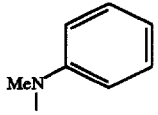 | >100 | 0.2 |
| 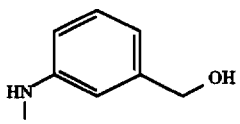 | >10–<100 | — |
| 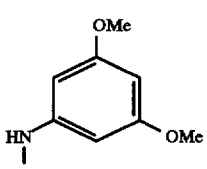 | ≦1 | ≈3 |
| 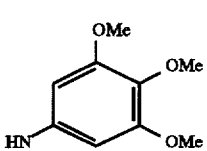 | 0.5 | ≦0.5 |
| 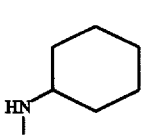 | >10–<100 | <1.0 |
| 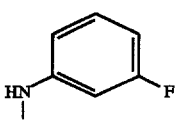 | 10 | 0.025 |
| 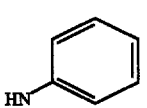 | 10 | 0.050 |
| 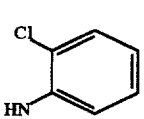 | 10 | ≈0.05 |
| 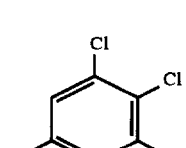 | >100 | ≈1.0 |

-continued

| Structure (R group on HN–) | | |
|---|---|---|
| 2-naphthyl | 10–50 | 0.050 |
| 1-naphthyl | ≦5 | 0.01 |
| 2,3-dihydro-1,4-benzodioxin-6-yl | 50 | — |
| 1H-pyrazol-3-yl | 20 | — |
| 2,3-dihydro-1H-inden-5-yl | 50 | — |
| 4-hydroxyphenyl | 3 | 0.1 |
| 4-methoxyphenyl | 10 | — |
| 3-nitrophenyl | 50 | — |
| 3-cyanophenyl | 10 | 10 |
| 3-benzoylphenyl | >100 | — |

-continued

| Structure | Ick activity IC$_{50}$ (μM) | EGF activity IC$_{50}$ (μM) |
|---|---|---|
| 3-(methoxycarbonyl)phenyl-NH– | >100 | — |
| 4-(isopropoxy)phenyl-NH– | 10 | 5 |
| 3,4-dimethoxyphenyl-NH– | 10 | — |
| 4-acetamidophenyl-NH– | >100 | — |
| 4-sulfamoylphenyl-NH– | 100 | — |
| 3,5-dimethoxybenzyl-NH– | >100 | — |
| benzyl-NH– | 20 | — |

| R = 3,4,5-trimethoxyphenyl | Ick activity IC$_{50}$ (μM) | EGF activity IC$_{50}$ (μM) |
|---|---|---|
| 6,7-dimethoxyquinazolin-4-yl-NH– | 0.5 | ≦0.5 |
| 5,8-dimethylquinazolin-4-yl-NH– | >100 | — |

-continued

| Structure | | |
|---|---|---|
| 3,4,5-trimethoxyphenyl amidine-formamidine structure | >100 | — |
| 4,5-dimethoxyphenyl with chloroformamidine | >100 | — |
| 6-methoxyquinazoline-NH structure | 10 | ≈5 |

| Structure  6,7-dimethoxyquinazoline core | Ick activity IC$_{50}$ (μM) | EGF activity IC$_{50}$ (μM) |
|---|---|---|
| 3-chlorophenoxy | 1 | 0.02 |
| 3-chlorophenylthio | 2.5 | 0.1 |
| 3-methoxyphenylthio | 5 | 2 |
| 2,3,5-trimethoxyphenyl (OMe, OMe, OMe) | 5 | — |

-continued

| Structure | Ick | CSF-R | PDGF-R | EGF-R |
|---|---|---|---|---|
| 6,7-dimethoxyquinazoline with HN-(3,4,5-trimethoxyphenyl) | 0.5 | >100 | 5–20 | 0.5 |
| 6,7-dimethoxyquinazoline with HN-(1-naphthyl) | 2.5 | 20 | >10 | 0.01 |
| 6,7-dimethoxyquinazoline with MeN-phenyl | >100 | 0.35 | 15 | 4.0 |
| 6,7-dimethoxyquinazoline with HN-(3-chlorophenyl) | 5 | >10 | 10 | 0.03 |

| 4-Substituted-6,7-dimethoxyquinazolines | Ick | CSF-R | PDGF-R | EGF-R |
|---|---|---|---|---|
| O-(3-chlorophenyl) | 1 | >50 | — | 0.02 |
| S-(3-chlorophenyl) | 2.5 | 3 | >50 | 0.1 |
| S-(3-methoxyphenyl) | 5 | <2 | — | 2 |

-continued
| | | | | |
|---|---|---|---|---|
|  | >100 | 0.35 | 15 | 4.0 |
|  | 10 | >50 | 10 | 0.05 |
|  | >10 | <2 | 25 | >50 (0.16) |
|  | 100 | 7 | — | 0.5 |
| 4-substituted-6,7-dimethoxyquinazolines | | | | |
|---|---|---|---|---|
| | Lck | CSF-R | PDGF-R | EGF-R |
|  | 50 | ≧50 | | — |
| 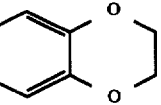 | 20 | >50* | | — |
|  | 2.5 | 3 | >50 | 0.1 |
| 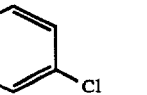 | 50 | >50 | | — |
| 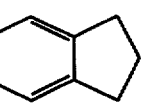 | 5 | <2 | — | 2 |
| 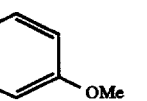 | 3 | >50* | | 0.1 |

-continued

| Structure | | | |
|---|---|---|---|
| 4-OMe anilino | 10 | >50* | — |
| 3-NO₂ anilino | 50 | >50* | — |
| 3-CN anilino | 10 | >50* | 10 |
| 3-benzoyl anilino | >100 | >50 | — |
| 3-(methoxycarbonyl) anilino | — | >50 | — |
| 4-isopropoxy anilino | 10 | 7* | 5 |
| 3,4-dimethoxy anilino | 10 | >20* | — |
| 4-acetamido anilino | >100 | >20* | — |
| 4-sulfamoyl anilino | 100 | >20; <2* | — |
| 2,3,5-trimethoxyphenyl | 5 | — | — |

-continued

| Structure | | |
|---|---|---|
| HN-CH2-C6H3(OMe)(OMe) (3,5-dimethoxybenzyl) | >100 | — | — |
| HN-CH2-C6H4-OMe (4-methoxybenzyl) | >100 | — | — |
| HN-CH2-C6H5 (benzyl) | 20 | >50* | — |

The results obtained by the above experimental methods evidence the useful protein tyrosine kinase inhibition properties of compounds within the scope of the present invention and possess therapeutic value as cellular antiproliferative agents. The above pharmacological test results may be used to determine the dosage and mode of administration for the particular therapy sought.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the for must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and if necessary, will be increased by small increments until the optimum effect under the circumstances is reached. The therapeutic human dosage, based on physiological studies using rats, will generally be from about 0.01 mg to about 100 mg/kg of body weight per day or from about 0.4 mg to about 10 g or higher although it may be administered in several different dosage units from once to several times a day. Oral administration requires higher dosages.

We claim:

1. A method of inhibiting cell proliferation in a patient suffering from a disorder characterized by such proliferation comprising administering to a patient a compound of the formula:

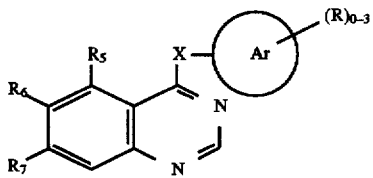

wherein

Ar is selected from substituted or unsubstituted phenyl, α-naphthyl, β-naphthyl, indazolyl, indanyl, pyrazolyl, pyridinyl, indol-3-yl, benzodioxan-6-yl, 1,2,3,4-tetrahydroquinolin-1-yl, or 2,3-dihydroindol-1-yl where the substituents may be located at any appropriate position of the ring system and are described by R;

X is a bond, O, S, NHCH$_2$ or NR$_4$;

R independently includes hydrogen, alkyl, hydroxy, alkoxy, phenyl, aralkyl, alkylsulphonyl, haloalkyl or halo;

R$_5$ is hydrogen or alkoxy;

R$_6$ and R$_7$ are alkoxy; and

R$_4$ is hydrogen, methyl, ethyl or benzyl; or a pharmaceutically acceptable salt thereof.

2. The method according to claim 1 wherein the compound is selected from the group consisting of:

4-(3,4,5-trimethoxyphenylamino)-6,7-dimethoxyquinazoline, 4-(N-methyl-3,4,5-trimethoxyanilino)-6,7-dimethoxyquinazoline, 4-(N-methyl-4-methoxyanilino)-6,7-dimethoxyquinazoline, 4-(N-methyl-4-chloroanilino)-6,7-dimethoxyquinazoline, (6,7-dimethoxyquinazolin-4-yl)methyl-(3-trifluoromethylphenyl)amine, (3-chlorophenyl)-(6,7-dimethoxyquinazolin-4-yl) methylamine, N-phenyl-N-(6,7,8-dimethoxyquinazolin-4-yl) methylamine, benzyl-(6,7-dimethoxyquinazolin-4-yl)phenylamine, (3-chlorophenyl)-(6,7-dimethoxyquinazolin-4-yl) ethylamine, (6,7-dimethoxyquinazolin-4-yl) methyl-p-tolyl-amine, (4-methoxybenzyl)-(6,7-dimethoxyquinazolin-4-yl) amine, (3,5-dimethoxybenzyl)-(6,7-dimethoxyquinazolin-4-yl) amine, 4-(pyrazol-3-ylamino)-6,7-dimethoxyquinazoline, and 6,7-dimethoxy-4-(N-methylanilino)quinazoline; or a pharmaceutically acceptable salt thereof.

3. The method according to claim 1 wherein the compound is 4-(pyrazol-3-ylamino)-6,7-dimethoxyquinazoline or a pharmaceutically acceptable salt thereof.

4. The method according to claim 1 wherein the compound is selected from the group consisting of:

(6,7-dimethoxyquinazolin-4-yl)-5-indazolylamine,

4-[N-(5-indanyl)amino]-6,7-dimethoxyquinazoline, 4-(3,6-dioxananilino)-6,7-dimethoxyquinazoline, 6,7-dimethoxy-4-(α-naphthylamino)quinazoline, and 6,7-dimethoxy-4-(β-naphthylamino)quinazoline; or a pharmaceutically acceptable salt thereof.

5. The method according to claim 1 wherein the compound is selected from the group consisting of:

4-(3,4,5-trimethoxyphenoxyl)-6,7-dimethoxyquinazoline, 4-(3-methoxythiophenoxy)-6,7-dimethoxyquinazoline, 4-(3-chlorothiophenoxy)-6,7-dimethoxyquinazoline, and 4-(3-chlorophenoxy)-6,7-dimethoxyquinazoline; or a pharmaceutically acceptable salt thereof.

6. The method according to claim 1 wherein the compound is selected from the group consisting of:

4-(4-hydroxyphenyl)-6,7-dimethoxyquinazoline, 4-(naphthalen-1-yl)-6,7-dimethoxyquinazoline, 4-(naphthalen-2-yl)-6,7-dimethoxyquinazoline, 4-(3-fluoro-4-methoxyphenyl)-6,7-dimethoxyquinazoline, 4-(3-phenylphenyl)-6,7-dimethoxyquinazoline, 4-(2-methoxypyridin-5-yl)-6,7-dimethoxyquinazoline, 4-(1-benzylindol-3-yl)-6,7-dimethoxyquinazoline, 4-(indol-3-yl)-6,7-dimethoxyquinazoline, 4-(1-methylindol-3-yl)-6,7-dimethoxyquinazoline, 4-(1-methylsulphonylindol-3-yl)-6,7-dimethoxyquinazoline, (±)-4-(2-methyl-1,2,3,4-tetrahydroquinolin-1-yl)-6,7-dimethoxyquinazoline, 4-(1,2,3,4-tetrahydroquinolin-1-yl)-6,7-dimethoxyquinazoline, and 4-(2,3-dihydroindol-1-yl)-6,7-dimethoxyquinazoline; or a pharmaceutically acceptable salt thereof.

7. A compound selected from the group consisting of:

4-(3,4,5-trimethoxyphenylamino)-6,7-dimethoxyquinazoline, 4-(N-methyl-3,4,5-trimethoxyanilino)-6,7-dimethoxyquinazoline, 4-(N-methyl-4-methoxyanilino)-6,7-dimethoxyquinazoline, 4-(N-methyl-4-chloroanilino)-6,7-dimethoxyquinazoline, (6,7-dimethoxyquinazolin-4-yl)methyl-(3-trifluoromethylphenyl)amine, (3-chlorophenyl)-(6,7-dimethoxyquinazolin-4-yl)methylamine, N-phenyl-N-(6,7,8-trimethoxyquinazolin-4-yl)methylamine, (3-chlorophenyl)-(6,7-dimethoxyquinazolin-4-yl)ethylamine, (6,7-dimethoxyquinazolin-4-yl)methyl-p-tolyl-amine, (4-methoxybenzyl)-(6,7-dimethoxyquinazolin-4-yl)amine, (3,5-dimethoxybenzyl)-(6,7-dimethoxyquinazolin-4-yl)amine, and 6,7-dimethoxy-4-(N-methylanilino)quinazoline; or a pharmaceutically acceptable salt thereof.

8. A compound which is 4-(pyrazol-3-ylamino)-6,7-dimethoxyquinazoline or a pharmaceutically acceptable salt thereof.

9. A compound selected from the group consisting of:

(6,7-dimethoxyquinazolin-4-yl)-5-indazolylamine,

4-[N-(5-indanyl)amino]-6,7-dimethoxyquinazoline, 4-(3,6-dioxananilino)-6,7-dimethoxyquinazoline, 6,7-dimethoxy-4-(α-naphthylamino)quinazoline, and 6,7-dimethoxy-4-(β-naphthylamino)quinazoline; or a pharmaceutically acceptable salt thereof.

10. A compound selected from the group consisting of:

4-(3,4,5-trimethoxyphenoxy)-6,7-dimethoxyquinazoline, 4-(3-methoxythiophenoxy)-6,7-dimethoxyquinazoline, 4-(3-chlorothiophenoxy)-6,7-dimethoxyquinazoline, and 4-(3-chlorophenoxy)-6,7-dimethoxyquinazoline; or a pharmaceutically acceptable salt thereof.

11. A compound selected from the group consisting of:

4-(4-hydroxyphenyl)-6,7-dimethoxyquinazoline, 4-(naphthalen-1-yl)-6,7-dimethoxyquinazoline, 4-(naphthalen-2-yl)-6,7-dimethoxyquinazoline, 4-(3-fluoro-4-methoxyphenyl)-6,7-dimethoxyquinazoline, 4-(3-phenylphenyl)-6,7-dimethoxyquinazoline, 4-(2-methoxypyridin-5-yl)-6,7-dimethoxyquinazoline, 4-(1-benzylindol-3-yl)-6,7-dimethoxyquinazoline, 4-(indol-3-yl)-6,7-dimethoxyquinazoline, 4-(1-methylindol-3-yl)-6,7-dimethoxyquinazoline, 4-(1-methylsulphonylindol-3-yl)-6,7-dimethoxyquinazoline, (±)-4-(2-methyl-1,2,3,4-tetrahydroquinolin-1-yl)-6,7-dimethoxyquinazoline, 4-(1,2,3,4-tetrahydroquinolin-1-yl)-6,7-dimethoxyquinazoline, and 4-(2,3-dihydroindol-1-yl)-6,7-dimethoxyquinazoline; or a pharmaceutically acceptable salt thereof.

12. A compound according to claim 9 which is 6,7-dimethoxy-4-(α-naphthylamino)quinazoline or a pharmaceutically acceptable salt thereof.

13. A compound according to claim 11 which is 6,7-dimethoxy-4-(1-methylsulphonylindol-3-yl)quinazoline or a pharmaceutically acceptable salt thereof.

14. A compound according to claim 11 which is 4-(1-benzylindol-3-yl)-6,7-dimethoxyquinazoline or a pharmaceutically acceptable salt thereof.

* * * * *

UNITED STATES PATENT AND TRADEMARK OFFICE
CERTIFICATE OF CORRECTION

PATENT NO. : 5,710,158
DATED : January 20, 1998
INVENTOR(S) : Michael R. Myers, et al.

It is certified that error appears in the above-identified patent and that said Letters Patent is hereby corrected as shown below:

On the title page, should read:

[63] Contiuation-in-part of Ser. No. 166,199, Dec. 10, 1993, Pat. No. 5,480,883, which is a continuation-in-part of Ser. No. 988,515, Dec. 10, 1992, abandoned, which is a continuation-in-part of Ser. No. 698,420, May 10, 1991, abandoned, and a continuation-in-part of Ser. No. 146,072, Nov. 8, 1993, Pat. No. 5,409,930.

Signed and Sealed this

Twentieth Day of October, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.     : 5,710,158
DATED          : January 20, 1998
INVENTOR(S)    : Michael R. Myers, et. al.

It is certified that error appears in the above-identified patent and that said Letters Patent is hereby corrected as shown below:

On the title page, item [63], should read:
Continuation-in-part of Ser. No. 166,199, Dec. 10, 1993, Pat. No. 5,480,883, which is a continuation-in-part of Ser. No. 988,515, Dec. 10, 1992, abandoned, which is a continuation-in-part of PCT US92/03736, May 6, 1992, which is a continuation-in-part of Ser. No. 698,420, May 10, 1991, abandoned.

Signed and Sealed this

Twenty-eighth Day of September, 1999

Attest:

Q. TODD DICKINSON

*Attesting Officer*     *Acting Commissioner of Patents and Trademarks*